United States Patent [19]
Ryan

[11] Patent Number: 5,196,182
[45] Date of Patent: Mar. 23, 1993

[54] TISSUE FIXATIVE

[75] Inventor: Wayne L. Ryan, Omaha, Nebr.

[73] Assignee: Streck Laboratories, Inc., Omaha, Nebr.

[21] Appl. No.: 696,926

[22] Filed: May 8, 1991

[51] Int. Cl.$^5$ .............................................. G01N 1/28
[52] U.S. Cl. ........................................ 424/3; 424/75; 422/40
[58] Field of Search .................. 424/3; 514/406, 397, 514/398, 407

[56] References Cited

U.S. PATENT DOCUMENTS

| | | | |
|---|---|---|---|
| 4,578,282 | 3/1986 | Harrison | 422/57 |
| 4,882,284 | 11/1989 | Kirchanski et al. | 436/63 |
| 4,946,669 | 8/1990 | Siegfried et al. | 424/4 |

Primary Examiner—Allen J. Robinson
Assistant Examiner—Brian M. Burn
Attorney, Agent, or Firm—Larson and Taylor

[57] ABSTRACT

Tissue fixatives, such as diazolidinyl urea, which are free of aldehydes and toxic chemicals are described. When used, either in aqueous or alcoholic solutions, good tissue preservation is attained. In addition, tissue antigens are retained which makes the fixative useful for immunostaining procedures.

34 Claims, No Drawings

TISSUE FIXATIVE

BACKGROUND OF THE INVENTION

The present invention relates to compositions for the fixation of cells and tissues and to methods for the fixation of cells and tissues using as the fixing agents certain compounds.

The objective of tissue fixation is to provide as much detail of the cell as possible. To do this, it is necessary to maintain the cells in their original unaltered morphology so that maximum cellular detail is observed under the microscope. With the development of immunostaining there is also the requirement that the antigens of the cells are not altered by the method of fixation or stabilization. Although the microscope is the usual means for examining cells that are fixed and stained, they may also be examined by the laser or the flow cytometer. The flow cytometer is an important method for examining a large number of cells in a brief time.

The usual formulations for stabilization of cells contain one or more agents which react vigorously with the proteins of the cells to denature, coagulate and insolubilize the components of the cell. Typical of this type of agent is picric acid, mercuric ions, formaldehyde and glutaraldehyde. In addition, some less toxic compounds which can also denature and stabilize the proteins are acetic and formic acid. Unfortunately, the toxicity associated with these compounds renders their use less than satisfactory.

OBJECTS OF THE INVENTION

Thus, it is an object of the invention to provide a fixative solution for tissues and cells which has an extremely low toxicity yet meets all of the requirements of a model fixative.

Another object of the invention is to provide a fixative solution for tissues and cells that preserves tissues and cells and their cellular detail.

Yet another object of the invention is to provide a fixative solution that provides an unaltered antigenic surface for reaction with specific antibodies.

SUMMARY OF THE INVENTION

These and other objects of the invention are obtained by a fixative solution for tissues and cells comprising histological fixing amounts of at least one active agent selected from the group consisting of:
i) diazolidinyl urea
ii) imidazolidinyl urea
iii) dimethylol-5,5-dimethylhydantoin
iv) dimethylol urea
v) 2-bromo-2-nitropropane-1,3-diol; and
vi) quaternary adamantane (e.g. 1-(3-chloroallyl)-3,5,7-tri-aza-1-azoiadamantiane-chloride, N-(3-chloroallyl)-hexammonium chloride such as Dowicil 200; Dowicide Q; Preventol D1)
in a solvent selected from water and an alcohol and mixtures thereof.

In another aspect, the invention comprises an improvement in a method of fixing tissues and cells with a histological fixative wherein the histological fixative is an active agent selected from at least one of the group consisting of:
i) diazolindinyl urea
ii) imidazolidinyl urea
iii) dimethylol-5,5-dimethylhydantoin
iv) dimethylol urea
v) 2-bromo-2-nitropropane-1,3-diol; and
vi) quaternary adamantane.

Unlike the typical histological fixing agents, the active agents of the invention have extremely low toxicity. For example, toxicity studies comparing diazolidinyl urea of the invention with formaldehyde of the prior art show the following:

|  | Inhalation Toxicity | Dermal Toxicity | LD 50 |
| --- | --- | --- | --- |
| Formaldehyde | 500 mg/Kg | 270 mg/Kg | 800 mg/Kg |
| Diazolidinyl urea | None | 2000 mg/Kg | 2570 mg/Kg |

This reduced toxicity makes disposal and handling less of a problem. In addition, since there is no inhalation toxicity, there are no badge detection devices required as there are for formaldehyde.

Another advantage offered by the active agents of the invention is the fact that they are not flammable and therefore do not present a fire hazard as do many of the prior art fixatives.

The mechanism by which the active agents of the invention provide the desired tissue and cell membrane is not known for certain. It is believed that the active agent binds in some fashion to the cell membrane or tissue to stabilize. This hypothesis is drawn because many of the active agents of the invention are known disinfectants which kill bacteria by binding to cell structures. This is not a full explanation of the mechanism responsible for the results of the invention since many other disinfectants such as Kathon and Omadine fail to provide tissue and cell stabilizing effects.

The ability of the active agents of the invention to preserve antigens is also not understood but it is probably due to a difference in the reaction between the active agents of the invention and prior art fixatives such as formaldehyde with proteins. Formaldehyde crosslinks with itself and proteins to obscure the antigen. To determine if this is true, diazolidinyl urea was added to the protein albumin to stabilize it. After incubation of diazolidinyl urea and protein mixture for 24 hours, disc-gel electrophoresis indicated no change in the rate of migration of the protein. When this experiment is conducted with formaldehyde, a large number of multimers and insoluble protein results.

In another aspect of the invention, it has been found that the addition of alkali metal salts of ascorbic acid increases the activity of the active agents of the invention in fixing the tissue or cell membrane.

DETAILED DESCRIPTION OF THE INVENTION

The fixative solutions of the invention are comprised of the active agents in solvent selected from water, an alcohol and mixtures thereof.

The alcohol solvent comprises one or more alkanols such as methanol, ethanol, propanol and butanol; polyols, e.g. diols or triols such as ethylene glycol, glycerol, propylene glycol and trimethylene glycol and mixtures of alkanols and polyols.

Whether the solvent employed is water, alcohol solvent or a mixture thereof depends principally upon the tissue or membrane being fixed. For example, where large pieces of tissue are being fixed, it is preferred to use an alcohol solvent or aqueous alcohol solvent since the alcohol solvents increase penetration. Also, in fixing cells such as Pap smears, the alcoholic preparations are preferred because they cause the cells to stick to the slides. When aqueous alcoholic solutions are employed as the solvent for the active agents of the invention, the ratio of alcohol to water will fall in the range of 4:1 to 2:1.

The amount of the active agents in the formulation of the invention is that effective to fix or stabilize the tissue or cell membrane. Generally, this amount falls in the range of abut 20 to 100 grams per liter, preferably 50 to 75 grams per liter.

When alkali metal ascorbic acid salts such as sodium ascorbate are included to increase the activity of the active agents to fix the tissue or cells, they are added in an amount of about 0.25 to 1 grams per liter.

The solute in the preparations of the invention may also include any of the other addendum conventionally added to histological fixative preparations. These addendum include mordants, buffers, penetration increasers, osmotically active substances and nuclear detail improvers and nuclear size increasers.

Examples of suitable mordants are salts with a metal ion having an oxidation state of two or more. Illustrative are zinc, strontium, calcium, barium and chromium salts. The preferred salt is zinc sulfate.

Suitable buffers include alkali metal phosphate salts such as sodium phosphate and potassium phosphate.

Osmotically active substances that may be included in the formulation of the invention are alkali metal salts such as sodium chloride. In addition, sugars such as the polysaccharides, sucrose, glucose and the like may be employed.

Nuclear detail improvers and nuclear size increasers include acetic acid and lithium salts such as lithium chloride. Zinc salts such as zinc sulfate not only improve nuclear definition but also improves staining.

Illustrative of substances which increase the rate of penetration of the fixing agent are dimethylsulfoxide and ethanol.

The following examples are illustrative of formulations of the invention.

EXAMPLE I

| | |
|---|---|
| Diazolidinyl urea | 50 g/L |
| Na₂HPO₄ | 0.73 g/L |
| KHPO₄ | 0.02 g/L |
| NaCl | 8.50 g/L |
| Distilled H₂O to one liter | |

EXAMPLE II

| | |
|---|---|
| Diazolidinyl urea | 50 g/L |
| Ethanol | 500 ml |
| Acetic acid, conc. | 10 ml |
| Distilled H₂O to one liter | |

EXAMPLE III

| | |
|---|---|
| Diazolidinyl urea | 50 g/L |
| Lithium chloride | 6.35 g/L |
| Distilled H₂O to one liter | |

EXAMPLE IV

| | |
|---|---|
| Diazolidinyl urea | 50 g/L |
| Dimethylsulfoxide | 100 ml |
| Distilled H₂O to one liter | |

EXAMPLE V

| | |
|---|---|
| Diazolidinyl urea | 50 g/L |
| Dimethylsulfoxide | 100 ml |
| Zinc chloride | 5.8 g/L |
| Distilled H₂O to one liter | |

EXAMPLE VI

| | |
|---|---|
| Diazolidinyl urea | 50 g/L |
| Ascorbic acid, sodium | .25 g/L |
| Distilled H₂O to one liter | |

The following is an example of the use of fixatives of the invention.

EXAMPLE VII

Tissue is immersed in the fixative of Example I for four hours. The treated tissue is then dehydrated through a series of graded alcohols, cleared in xylene and impregnated with molten paraffin. This procedure is performed under heat and vacuum/pressure in a 12-hour cycle using a Fisher Histomatic (Model 166 MP) tissue processor. The tissue is then blocked, paraffin embedded, rehydrated in ice water for a minimum of three hours to enhance sectioning, and sectioned at 4-5 microns. The tissue is mounted on a glass slide, deparaffinized, stained, coverslipped and evaluated microscopically.

The following example demonstrates the satisfactory results obtained with the fixative of the invention using various staining methods.

EXAMPLE VIII

Example VII is repeated using the staining method identified. The results in each case are as follows:

| Staining Method | Results |
|---|---|
| Mayer's mucicarmine | Demonstrable; well-defined |
| Elastin | Satisfactory detail |
| Movat's reticulin stain | Satisfactory detail; minimal shrinkage |
| Gomori's trichrome stain | Fibrous tissue well-defined |
| Periodic Acid-Schiff (PAS) | Non-specific staining not evidenced as in formalin-fixed prep. |
| Geimsa | Satisfactory detail |
| Hematoxylineosin | Satisfactory detail |

The following example demonstrates the ability of the fixative of the invention in retaining tissue antigens in immunostaining procedures.

EXAMPLE IX

The tissues identified below having the antigenic sites identified below are fixed with the fixative formulation of Example I and immunohistochemically stained using avidin-biotin stainings.

| Tissue | Markers Detected |
|---|---|
| Lymph node | LN-1 |
| | LN-2 |
| | LN-3 |
| | UCA |
| | L-26 |
| | LCHL-1 |
| Brain | Neurofilament |
| | Glial Fibrillary Acidic Protein |
| Hodgkins node | Ber $H_2$ |
| | Leu $M_1$ |
| Colon | Cytokeratin MAK-6 |
| | Cytokeratin AE1/AE3 |
| Muscle | Desmin |
| Pituitary | S-100 |
| Thyroid | Thyroglobulin |
| Breast | α-lactalbumin |

None of the antigenic sites are affected by the immunostaining.

It is claimed:

1. A fixative solution for tissues and cells comprising histological fixing amounts of an active agent selected from the group consisting of:
   i) diazolidinyl urea
   ii) imidazolidinyl urea
   iii) dimethylol-5,5-dimethylhydantoin
   (iv) dimethylol urea
   (v) 2-bromo-2-nitropropane-1,3-diol; and
   (vi) quaternary adamantane
in a solvent selected from the group consisting of water, alcohol, dimethylsulfoxide and mixtures thereof, said active agent being present in an amount of about 20 to 100 grams per liter.

2. A fixative solution according to claim 1 wherein the active agent is diazolidinyl urea.

3. A fixative solution according to claim 1 wherein the active agent is imidazolidinyl urea.

4. A fixative solution according to claim 1 wherein the active agent is dimethylol-5,5-dimethylhydantoin.

5. A fixative solution according to claim 1 wherein the active agent is dimethylol urea.

6. A fixative solution according to claim 1 wherein the active agent is 2-bromo-2-nitropropane-1,3-diol.

7. A fixative solution according to claim 1 wherein the active agent is quaternary adamantane.

8. A fixative solution according to claim 1 wherein the active agent is present in an amount of about 20 to 100 grams per liter.

9. A fixative solution according to claim 1 wherein the solvent is water.

10. A fixative solution according to claim 1 wherein the solvent is an alcohol.

11. A fixative solution according to claim 10 wherein the alcohol is an alkanol.

12. A fixative solution according to claim 11 wherein the alkanol is ethyl alcohol.

13. A fixative solution according to claim 10 wherein the alcohol is a polyol.

14. A fixative solution according to claim 13 wherein the polyol is a diol.

15. A fixative solution according to claim 14 wherein the diol is ethylene glycol.

16. A fixative solution according to claim 1 including 0.25 to 1 grams per liter of an alkali metal salt of ascorbic acid.

17. A fixative solution according to claim 16 wherein the salt is sodium ascorbate.

18. A fixative solution according to claim 1 including acetic acid in an amount sufficient to improve nuclear detail.

19. A fixative solution according to claim 1 including dimethylsulfoxide in an amount sufficient to increase the rate of penetration of said active ingredient.

20. A fixative solution according to claim 1 including zinc sulfate in an amount sufficient to improve staining and nuclear detail.

21. In a method of fixing tissues or cells by treating same with a histological fixative, the improvement comprising employing as said histological fixative a composition comprising at least one of an active agent selected from the group consisting of:
   i) diazolidinyl urea
   ii) imidazolidinyl urea
   iii) dimethylol-5,5-dimethylhydantoin
   iv) dimethylol urea
   v) 2-bromo-2-nitropropane-1,3-diol; and
   vi) quaternary adamantane
in a solvent selected from water, an alcohol and mixtures thereof, said active agent being present in an amount of about 20 to 100 grams per liter.

22. In a method according to claim 21 wherein the active agent is diazolidinyl urea.

23. In a method according to claim 21 wherein the active agent is imidazolidinyl urea.

24. In a method according to claim 21 wherein the active agent is dimethylol-5,5-dimethylhydantoin.

25. In a method according to claim 21 wherein the active agent is dimethylol urea.

26. In a method according to claim 21 wherein the active agent is 2-bromo-2-nitropropane-1,3-diol.

27. In a method according to claim 21 wherein the active agent is quaternary adamantane.

28. The method according to claim 21 wherein the solvent is water.

29. The method according to claim 21 wherein the solvent is an alcohol.

30. The method according to claim 21 wherein the solvent includes 0.25 to 1 grams per liter of an alkali metal salt of ascorbic acid.

31. The method according to claim 30 wherein the salt is sodium ascorbate.

32. The method according to claim 21 wherein the solvent includes acetic acid in an amount sufficient to improve nuclear detail.

33. The method according to claim 21 wherein the solvent includes dimethylsulfoxide in an amount sufficient to increase the rate of penetration of said active ingredient.

34. The method according to claim 21 wherein the solvent includes zinc sulfate in an amount sufficient to improve staining and nuclear detail.

* * * * *